United States Patent [19]
Hilliard

[11] Patent Number: 5,586,551
[45] Date of Patent: Dec. 24, 1996

[54] OXYGEN MASK WITH NEBULIZER

[76] Inventor: Kenneth R. Hilliard, 2840 Gibbs-Williams Rd., Dallas, Tex. 75233

[21] Appl. No.: 503,327

[22] Filed: Jul. 17, 1995

[51] Int. Cl.$^6$ .................................................. A61M 11/00
[52] U.S. Cl. .................. 128/203.29; 128/200.14; 128/200.18; 128/200.21; 128/203.22; 128/203.28
[58] Field of Search ................ 128/200.14, 200.18, 128/200.21, 203.22, 203.28, 203.29, 204.11, 205.17

[56] References Cited

U.S. PATENT DOCUMENTS

| | | | |
|---|---|---|---|
| 1,693,730 | 12/1928 | Schröder | 128/203.13 |
| 2,012,441 | 8/1935 | Willson et al. | 128/205.25 |
| 3,182,659 | 5/1965 | Blount | 128/200.21 |
| 3,502,077 | 3/1970 | Joseph | 128/200.14 |
| 3,667,463 | 6/1972 | Barnes | 128/203.16 |
| 3,769,973 | 11/1973 | Esbenshade, Jr. | 128/200.14 |
| 3,894,537 | 7/1975 | Camp | 128/203.17 |
| 3,977,432 | 8/1976 | Vidal | 128/205.11 |
| 4,512,341 | 4/1985 | Lester | 128/200.21 |
| 4,702,243 | 10/1987 | Smith | 128/204.18 |
| 4,746,067 | 5/1988 | Svoboda | 128/200.18 |
| 4,865,027 | 9/1989 | Laanen et al. | 128/200.21 |
| 4,886,055 | 12/1989 | Hoppough | 128/200.14 |
| 4,926,855 | 5/1990 | Hellquist et al. | 128/206.15 |
| 4,938,209 | 7/1990 | Fry | 128/200.21 |
| 5,277,175 | 1/1994 | Riggs et al. | 128/200.21 |
| 5,318,015 | 6/1994 | Mansson et al. | 128/200.21 |
| 5,318,019 | 7/1994 | Celaya | 128/205.25 |

FOREIGN PATENT DOCUMENTS

| | | |
|---|---|---|
| 605207 | 5/1926 | France . |
| 319067 | 3/1957 | Switzerland . |
| WO82/00254 | 2/1982 | WIPO . |

*Primary Examiner*—V. Millin
*Assistant Examiner*—V. Srivastava
*Attorney, Agent, or Firm*—Richard C. Litman

[57] ABSTRACT

An oxygen mask having an extended nose region to accommodate openings for both a nebulizer and the main oxygen supply depended on by the patient for adequate respiration. The mask allows the nebulizer to be used without having to remove the patient from the main oxygen supply.

6 Claims, 6 Drawing Sheets

OXYGEN MASK WITH NEBULIZER

BACKGROUND OF THE INVENTION

1. Field of the Invention

The present invention relates to a respiratory therapy mask delivering both oxygen and an inhaled medication.

2. Description of the Prior Art

Patients having respiratory problems are often administered pure oxygen through a non-rebreather mask. Such patients, in addition, often will require inhaled medications. Such medications are most commonly administered using a device commonly known as a nebulizer. Nebulizers are powered by a low flow rate oxygen stream. In contrast, oxygen administered to patients through the non-rebreathing mask, is supplied at a high flow rate which is required by patients having respiratory difficulties. Inhaled medications are packaged, and dosage amounts are determined, for use with the commonly used, low flow rate nebulizer.

Heretofore, the practice has been to remove the non-rebreathing mask from the patients face and have the patient inhale the medication from the nebulizer. Because the gas stream from the nebulizer is deficient in oxygen, patients will experience some discomfort due to hypoxia and consequent shortness of breath. Therefore, the patient must be periodically switched from the nebulizer to the non-rebreathing mask and then back to the nebulizer. Obviously, in addition to being uncomfortable for the patient, this procedure is very inconvenient and time consuming for the healthcare personnel.

To overcome the aforementioned difficulties the present invention, which is a non-rebreathing mask incorporating a substantially standard nebulizer, was developed. Although devices that introduce medications into the inhaled oxygen stream are known in the prior art, none are seen to allow the convenient use of medication packages and dosage amounts developed for use with commonly used, low flow rate nebulizers, without having to modify the dosage amounts or have unused portions of medication left over.

U.S. Pat. No. 5,277,175, issued to Riggs et al., shows a nebulizer having a face mask. Riggs et al. do not show separate inlets to a mask for a nebulizer and an oxygen stream.

U.S. Pat. No. 4,886,055, issued to Hoppough, shows a nebulizer having a face mask. Hoppough does not show separate inlets to a mask for a nebulizer and an oxygen stream.

U.S. Pat. No. 4,865,027, issued to Laanen et al., shows a non-rebreathing mask with an aerosol delivery system. Laanen et al. do not show separate inlets to a mask for a nebulizer and an oxygen stream.

U.S. Pat. No. 3,977,432, issued to Vidal, shows an oxygen mask having an oxygen diluting device. Vidal does not show separate inlets to a mask for a nebulizer and an oxygen stream.

U.S. Pat. No. 3,894,537, issued to Camp, shows a nebulizer having a face mask. Camp does not show separate inlets to a mask for a nebulizer and an oxygen stream.

U.S. Pat. No. 3,769,973, issued to Esbenshade, Jr., shows a nebulizer in series with an oxygen supply to a mouth piece. Esbenshade, Jr. does not show separate inlets to a mask for a nebulizer and an oxygen stream.

U.S. Pat. No. 3,667,463, issued to Barnes, shows a mask for supplying anesthetic mixed in with an oxygen stream to a patient. Barnes does not teach or suggest separate inlets to a mask for a nebulizer and an oxygen stream.

U.S. Pat. No. 1,693,730, issued to Schröder, shows a mask for supplying anesthetic mixed in with an oxygen stream to a patient. Schröder does not teach or suggest separate inlets to a mask for a nebulizer and an oxygen stream.

Swiss Patent Document Number 319067, by Ledwina, shows a mask having an inlet for a nebulizer and a port for admission of water vapor to the mask. Ledwina does not teach or suggest separate inlets to a mask for a nebulizer and an oxygen stream.

International Patent Document Number WO 82/00254, by Rollins et al., shows an oxygen mask that allows for nasogastric intubation without having to remove the mask. Rollins et al. do not show an attachment for a nebulizer.

French Patent Document Number 605,207, by Sociáte Collin & Co., shows a mask for supplying anesthetic mixed in with an oxygen stream to a patient. French Document '207 does not teach or suggest separate inlets to a mask for a nebulizer and an oxygen stream.

Product literature AIRLIFE™ MISTY-NEB™ Nebulizer, Catalog No. 002038, Baxter Healthcare Corp., Pharmaseal Division, Valencia, Calif. circa 1995, by Baxter Healthcare Corp. shows a conventional nebulizer. This document does not show separate inlets to a mask for a nebulizer and an oxygen stream.

None of the above inventions and patents, taken either singly or in combination, is seen to describe the instant invention as claimed.

SUMMARY OF THE INVENTION

The present invention is directed to an oxygen mask having an extended nose region to accommodate openings for both a nebulizer and the main oxygen supply depended on by the patient for adequate respiration.

Accordingly, it is a principal object of the invention to allow the use of a nebulizer without having to remove the patient from the main oxygen supply.

It is another object of the invention to provide an oxygen mask incorporating a nebulizer which can be used as a conventional non-rebreathing mask when administration of an inhaled medication is no longer necessary.

It is a further object of the invention to provide an oxygen mask which can be used in conjunction with off-the-shelf nebulizers.

Still another object of the invention is to provide an oxygen mask incorporating a nebulizer, which allows medications packaged for use with conventional nebulizers to be utilized without having to modify recommended dosages or having unused portions of the medications left over.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
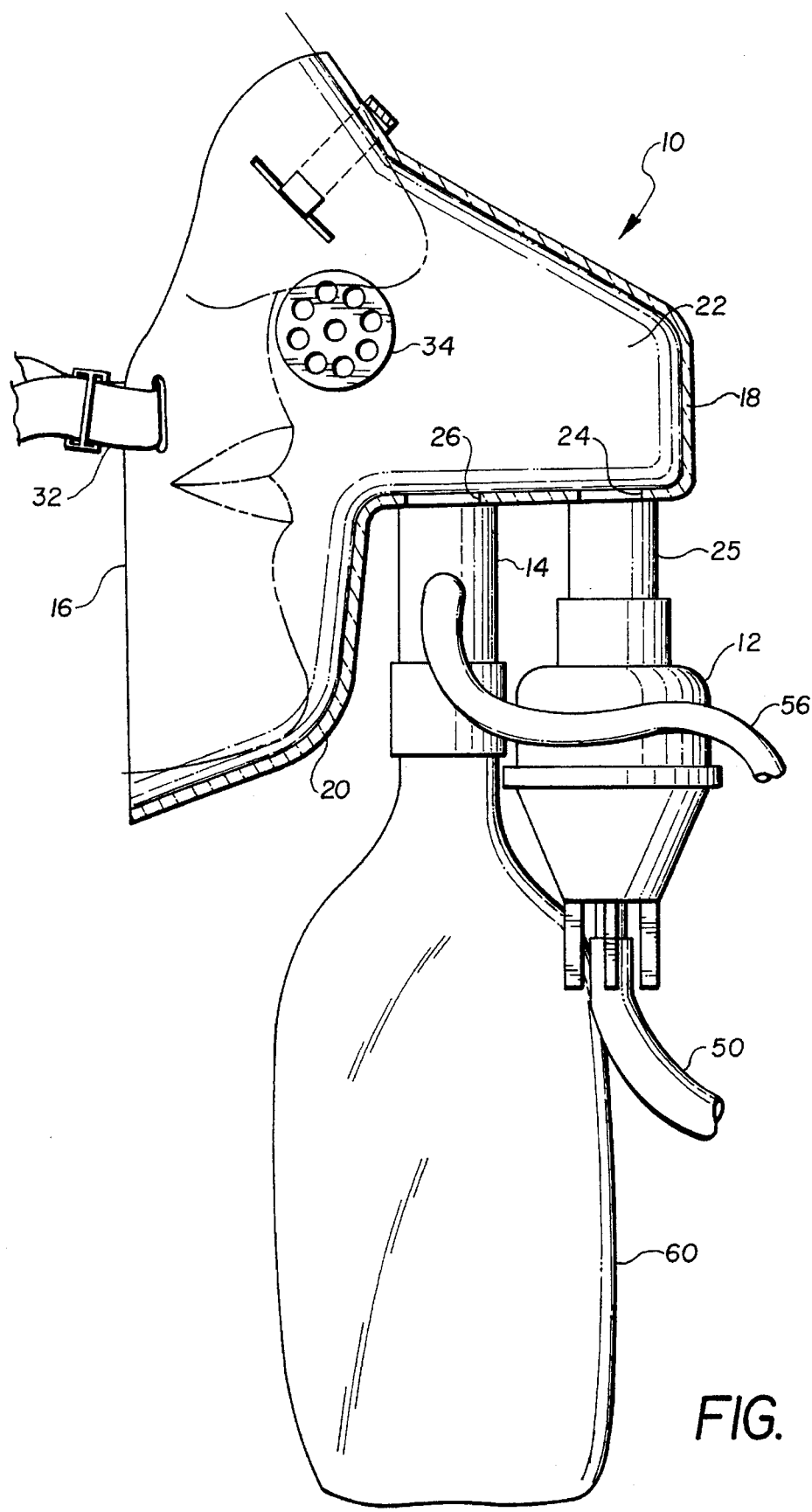
FIG. 1 is an environmental view of the oxygen mask of the present invention with the nebulizer attached.
Figure 2:
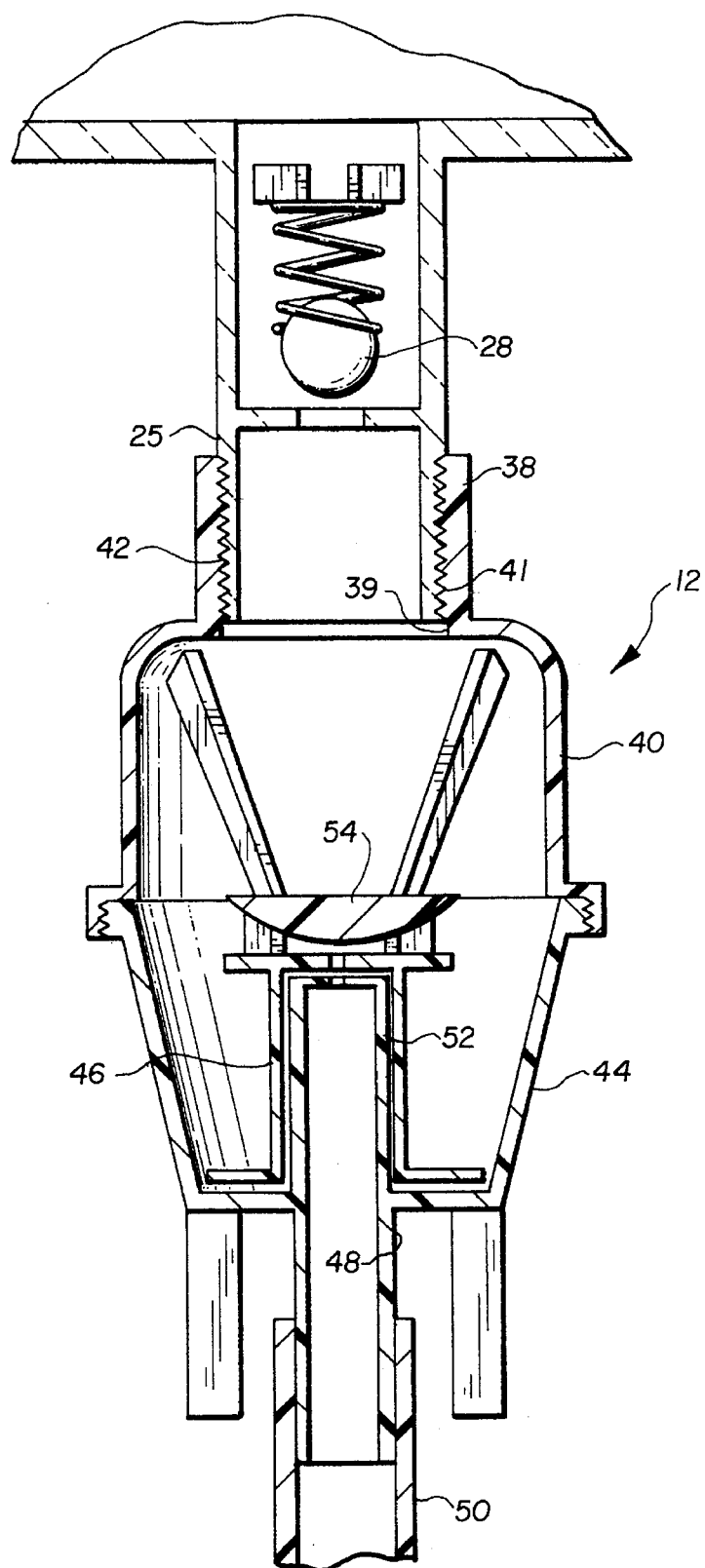
FIG. 2 is a fragmentary view in cross section showing internal details of the nebulizer and its attachment to the mask.
Figure 3:
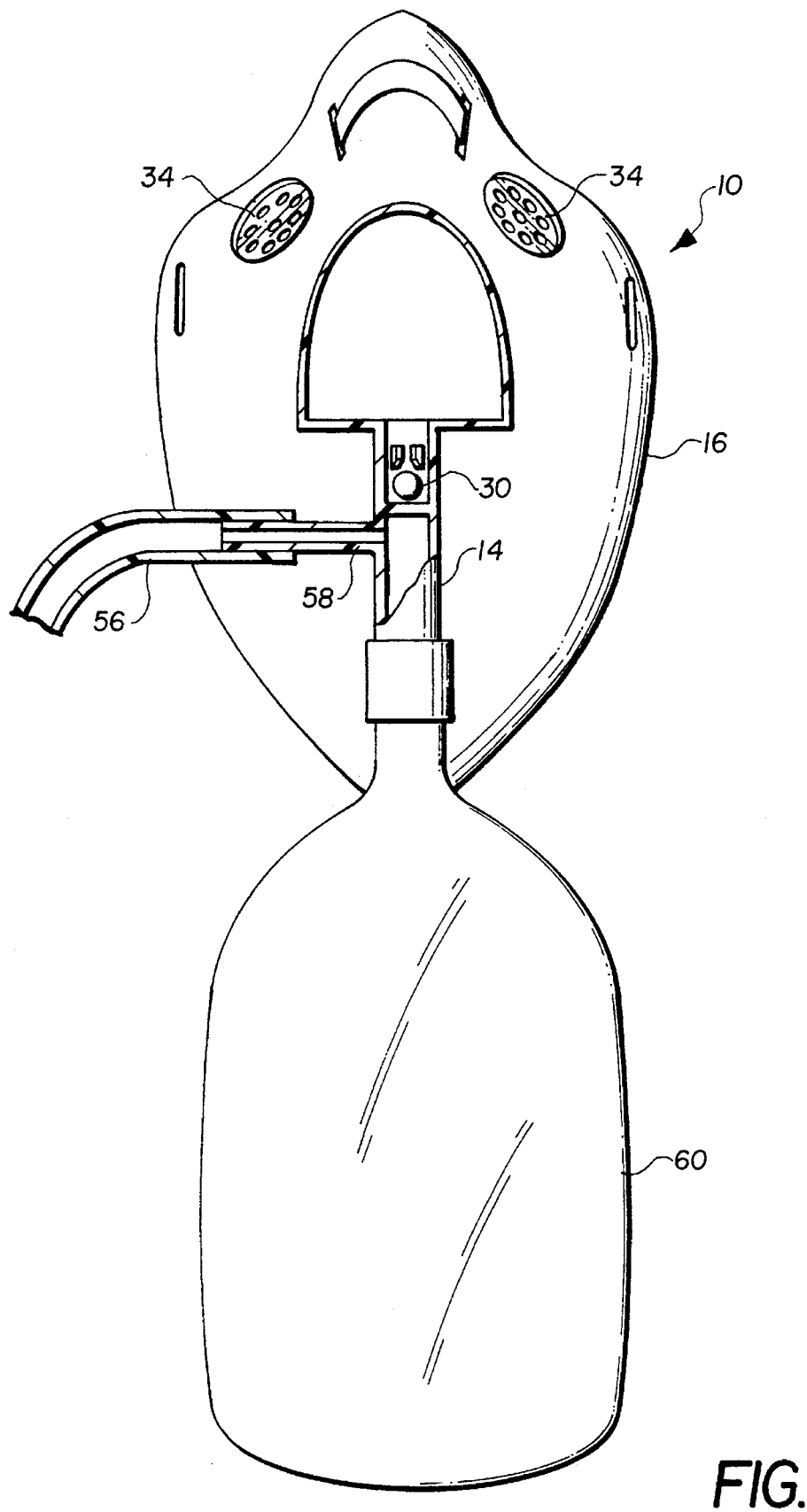
FIG. 3 is a front view of the oxygen mask of the present invention partially broken away to reveal details of the main oxygen supply assembly.
Figure 4:
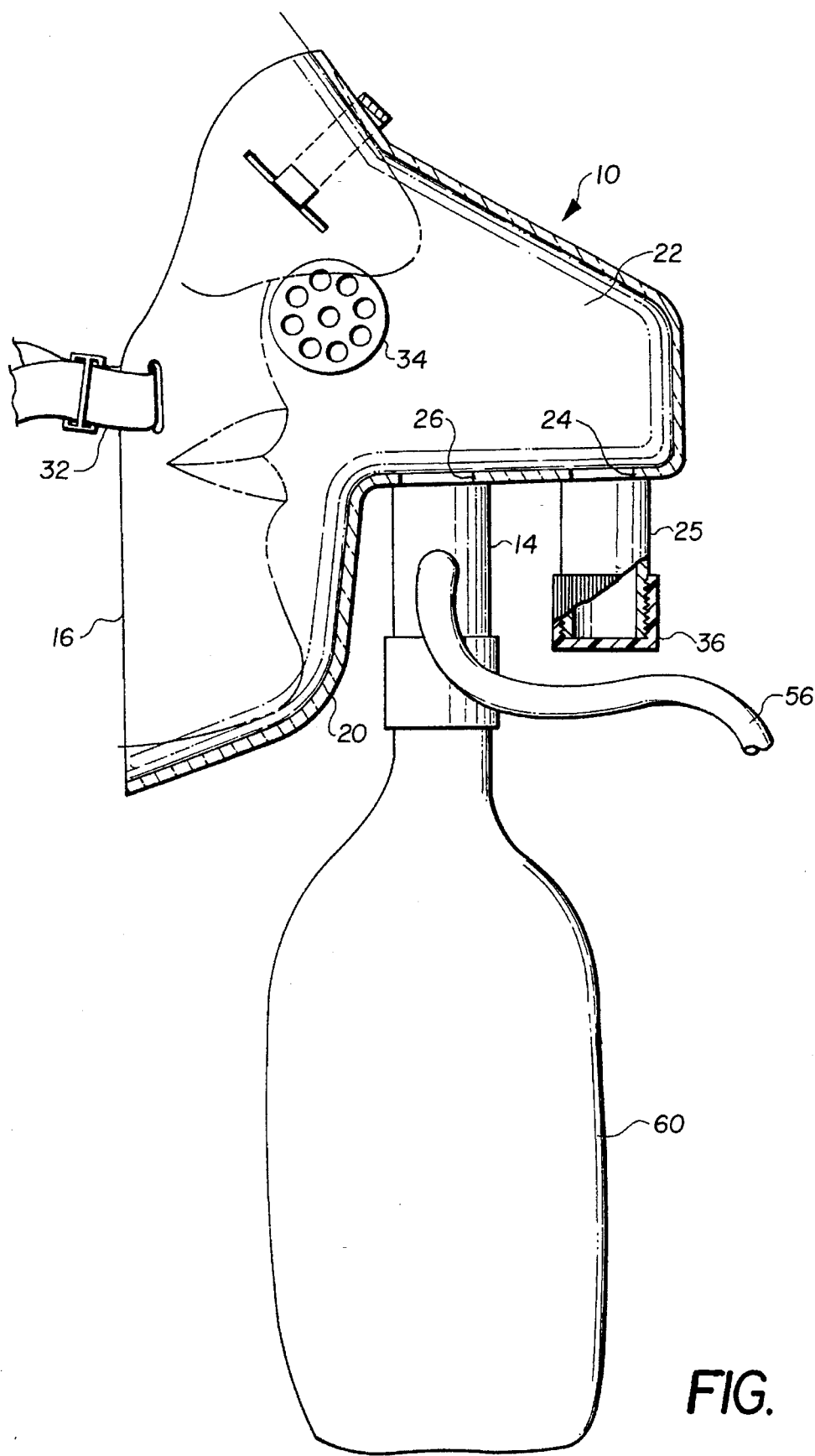
FIG. 4 is an environmental view of the oxygen mask of the present invention with the nebulizer replaced by a screw-on cap.

Referring to FIGS. 1–4, the present invention is a respiratory therapy mask 10 having a nebulizer 12 in addition to the main oxygen supply conduit 14. The mask portion 16 follows closely the construction of conventional non-rebreathing masks, except that the mask 16 has an extended nose region 18 to accommodate the openings for both the nebulizer and the main oxygen supply. Mask 16 is generally shaped to follow the contour of the face around the nose and mouth. The mask 16 has a chin projection 20 and a nose projection 18. The periphery of mask 16 sealingly abuts a wearer's face around the nose, mouth, and chin to form an enclosed space 22 in communication with the wearer's or patient's nose and mouth shown in dashed lines in FIGS. 1 and 4–6.

Openings 24 and 26 for both the nebulizer and the main oxygen supply are preferably provided with one-way valves 28 and 30. The valves 28 and 30 are only open when the patient is inhaling. Thus the main oxygen supply will not interfere with the patient's exhalation, and medication will not be wasted by being supplied during exhalation. Mask 16 has a strap 32 to retaining mask 16 on the patient's face. Also, exhalation ports 34 are provided in mask 16 to allow exhaled gases to pass to the atmosphere.

The one way valve 28 is preferably of the spring loaded type to ensure proper functioning in spite of medication residues that may adhere to and accumulate on the surfaces of the valve 28. The attachment 25 for the nebulizer is preferably threaded to allow the nebulizer to be removed when administration of the inhaled medication is no longer required. The opening of the nebulizer attachment 25 can the be capped by cap 36, thus converting mask 16 functionally to a conventional non-rebreathing mask.

The nebulizer 12 is similar in construction and operation to the MISTY-NEB™ nebulizer described in the product literature from Baxter Healthcare Corp. discussed above, except that the nebulizer 12 has a threaded portion 38 near the outlet 39 of the nebulizer connector 40 which matingly engages the complementary threads at the opening of the nebulizer attachment 25. In the example shown threaded portion 38 has female threads 41 and the nebulizer attachment 25 has male threads 42 provided adjacent the opening thereof.

Nebulizer 12 includes a nebulizer bottle 44, a jet housing 46 and a nebulizer connector 40. The nebulizer bottle 44 is a cup-shaped container in which the liquid medication is placed. The nebulizer bottle has an inlet 48 for the low flow rate oxygen supply tube 50. Protruding from the bottom of the nebulizer bottle is the jet 52 which receives the oxygen supplied through inlet 48. Jet housing 46 fits over jet 52. Nebulizer connector 40 can be threadably attached to the nebulizer bottle 44. Nebulizer connector 40 has a baffle 54 to disperse the gas issuing from Jet housing 46 and the medication entrained therein.

In operation the jet housing 46 is sized to leave a small annular gap between the jet 52 and the jet housing interior. Liquid medication (not shown), placed in the nebulizer bottle 44, is drawn up into this annular gap by capillary action. The liquid is drawn up all the way to the tip of jet 52, assisted by low pressure created by the oxygen jet issuing from the jet 52. When the liquid medication reaches the tip of the jet 52, it becomes entrained in the oxygen jet. Once the liquid medication is entrained in the gas stream, it is further dispersed by the baffle 54 before it passes to the inside of mask 16 and is inhaled by the patient.

The high flow rate oxygen supply to the mask 16 is regulated by the valve 30. Main oxygen supply 56 communicates with the main oxygen supply conduit 14 through the side inlet 58. When the patient exhales, valve 30 is closed. Oxygen from supply line 56 fills the bag 60. During inspiration, valve 30 opens allowing the oxygen filling bag 60 to be inhaled by the patient. Bag 60 allows the intermittent supply of oxygen to mask 16 without having to interrupt the continuous flow of oxygen through supply line 56.

Figure 5:
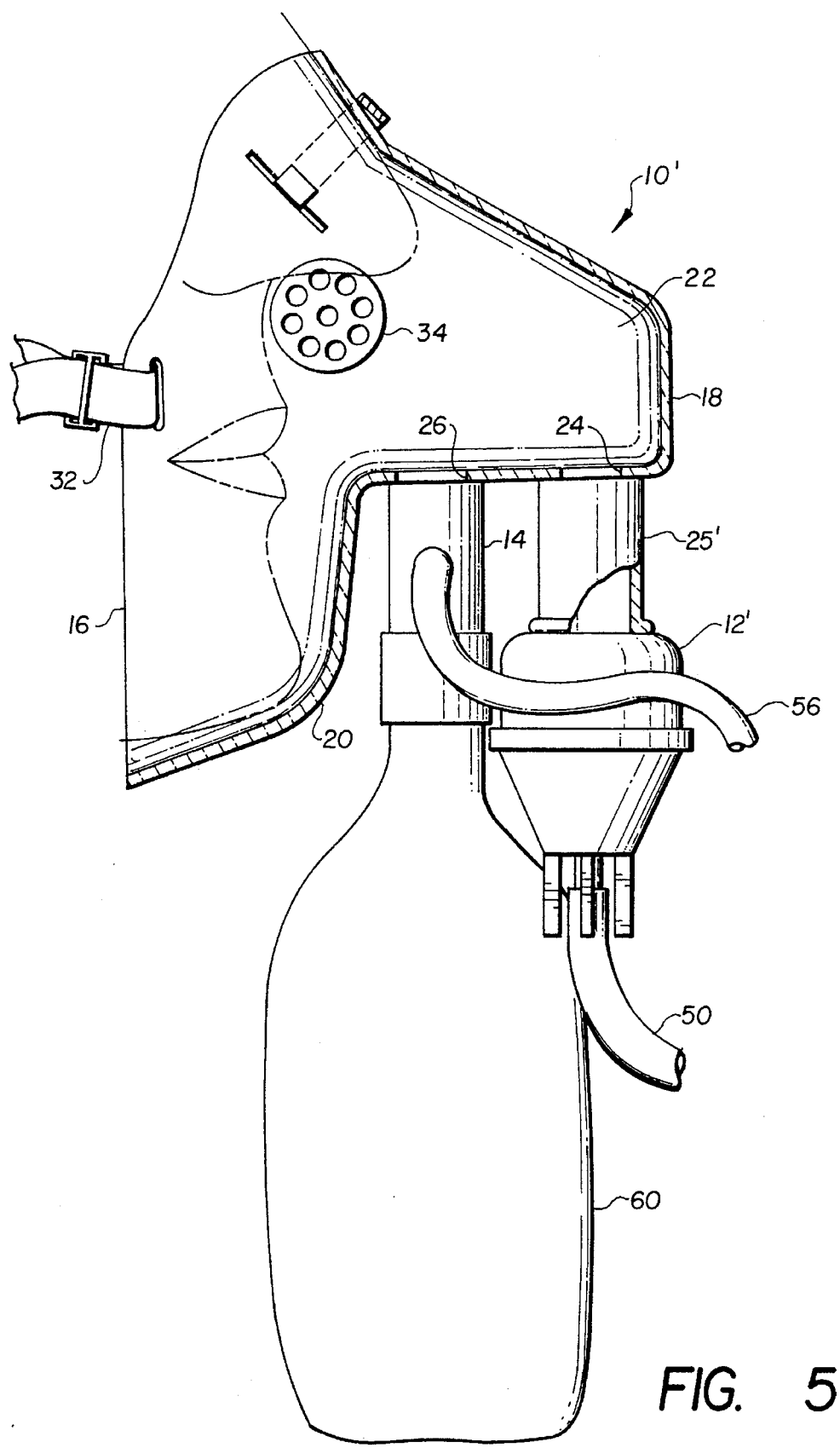
FIG. 5 is an environmental view of the oxygen mask of the present invention with the nebulizer attached by a friction fit.
Figure 6:
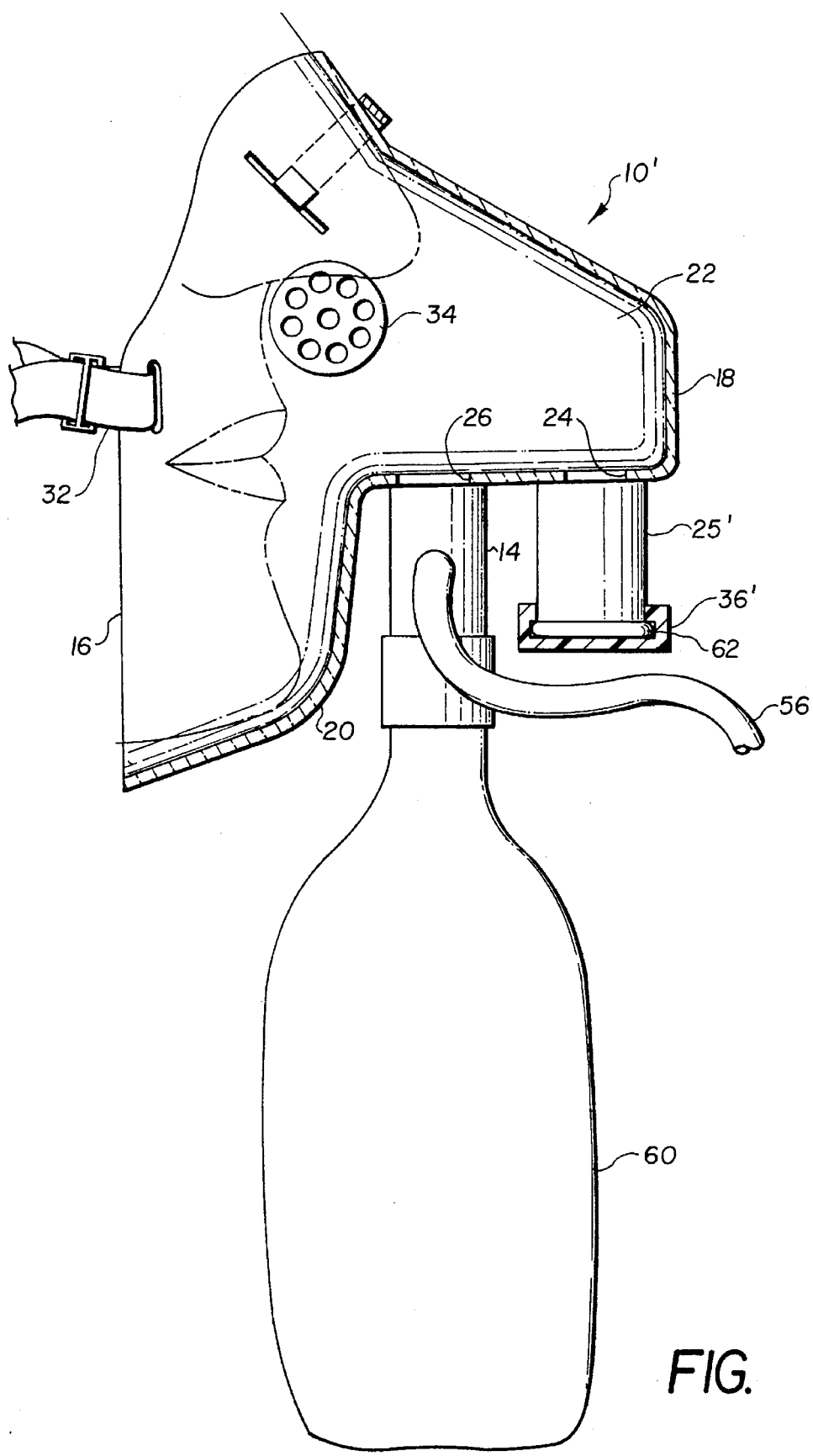
FIG. 6 is an environmental view of the oxygen mask of the present invention with the nebulizer replaced by a snap-on cap.

Referring to FIGS. 5 and 6, a second embodiment of the invention 10' is seen. In this embodiment the nebulizer 12' is attached to the nebulizer attachment 25' in FIG. 5 by a friction fit rather than the screw threads of the first embodiment. Also, in FIG. 6, cap 36 is replaced by cap 36' which is adapted to snap over the projecting lip 62 at the end of the nebulizer attachment 25'. This feature is provided for by making cap 36' from a sufficiently resilient material such as plastic. Nebulizer Attachment 25' allows off-the-shelf nebulizers to be used in conjunction with the mask 16, obviating the need for screw threads at the nebulizer cap outlet 39.

It should readily be apparent to those skilled in the art that, although the device of the present invention has been described in the context of providing oxygen to a patient, this description is provided by way of an example only and that the device of the present invention can also be used with other gases such as air or an oxygen and helium mixture.

It is to be understood that the present invention is not limited to the embodiments described above, but encompasses any and all embodiments within the scope of the following claims.

I claim:

1. A respiratory therapy mask comprising:

a mask portion defining a cavity having an opening, said cavity and said opening being dimensioned and configured for said opening to sealingly contact a patient's face and for said cavity to form an enclosed space about the patient's nose and mouth, said mask portion further having a first one-way inlet valve and a second one-way inlet valve;

a first main breathable gas supply assembly communicates with said first inlet valve for supplying a first breathable gas to a patient; and a nebulizer assembly removably attached to said second inlet valve and supplies an inhalable medication entrained in a second breathable gas to said mask portion, said nebulizer assembly includes:

a nebulizer bottle in the form of a container containing a jet with a centered nozzle, said nozzle receiving said second breathable gas from a secondary gas source, whereby the breathable gas from said secondary gas source issues as a jet stream;

a jet housing fitting over said jet and creating an annular gap between said jet housing and said jet, the inhalable medication in liquid form filling said annular gap and reaching the nozzle of said jet, the inhalable medication becomes being entrained in the breathable gas from said secondary gas source issuing from said nozzle; and a nebulizer connector removably attached to said nebulizer bottle, said nebulizer connector containing a baffle centered said nebulizer connector, said baffle which disperses the second breathable gas from said secondary gas source issuing from said nozzle and having inhalable medication entrained therein into the gas jet stream, and said nebulizer connector having an outlet in communication with said second inlet valve;

whereby a patient can receive a prescribed dosage of medication simultaneously with the first breathable gas to prevent hypoxia and shortness of breath.

2. The respiratory therapy mask according to claim 1, said first main breathable gas supply assembly includes a hollow cylindrical body having a first end and a second end, said hollow cylindrical body having a main gas supply inlet provided intermediate said first end of said hollow cylindrical body and said second end of said hollow cylindrical body, said first end of said hollow cylindrical body being in communication with said first inlet, and said second end of said hollow cylindrical body being in direct communication with a collapsible bag.

3. The respiratory therapy mask according to claim 2, said second inlet is defined by a conduit extending from said mask portion, said conduit having a first end in communication with said cavity and a second end in communication with said nebulizer, said nebulizer being removably attached to said second end of said conduit by a friction fit.

4. The respiratory therapy mask according to claim 3, wherein a cap is friction fit on the second end of said conduit when said nebulizer assembly is removed.

5. The respiratory therapy mask according to claim 4, wherein said second inlet is defined by a conduit extending from said mask portion, said conduit having a first end in communication with said cavity and a second end in communication with said nebulizer, said second end of said conduit having screw threads provided thereat to thereby allow removable attachment of said nebulizer.

6. The respiratory therapy mask according to claim 5, wherein a cap is threadably mounted on the second end of said conduit when said nebulizer assembly is removed.

* * * * *